United States Patent [19]

Zeugner et al.

[11] Patent Number: 4,505,908

[45] Date of Patent: Mar. 19, 1985

[54] 7-BROMO-5-(2-HALOPHENYL)-1H-2,3-DIHYDRO-1,4-BENZODIAZEPINE PHARMACEUTICALS

[75] Inventors: Horst Zeugner; Michael Ruhland; Hans Liepmann, all of Hannover; Wolfgang Milkowski, Burgdorf; Herbert Muesch, Wennigsen, all of Fed. Rep. of Germany

[73] Assignee: Kali-Chemie Pharma GmbH, Hannover, Fed. Rep. of Germany

[21] Appl. No.: 422,297

[22] Filed: Sep. 23, 1982

[30] Foreign Application Priority Data

Sep. 30, 1981 [DE] Fed. Rep. of Germany ....... 3138769

[51] Int. Cl.³ .................... A61K 31/55; C07D 243/16; C07D 487/04
[52] U.S. Cl. .............................. 514/221; 260/239 E; 260/239 BD
[58] Field of Search .................. 260/239 BD; 424/244

[56] References Cited

U.S. PATENT DOCUMENTS

| 3,998,809 | 12/1976 | Milkowski et al. | 260/340.3 |
| 4,096,141 | 6/1978 | Milkowski et al. | 260/239 |
| 4,098,786 | 7/1978 | Milkowski et al. | 260/239 |
| 4,244,869 | 1/1981 | Milkowski et al. | 260/239 |

Primary Examiner—Alton D. Rollins

Attorney, Agent, or Firm—Schwartz, Jeffery, Schwaab, Mack, Blumenthal & Koch

[57] ABSTRACT

Disclosed are 7-bromo-5-(2-halophenyl)-1H-2,3-dihydro-1,4-benzodiazepines of the formula I

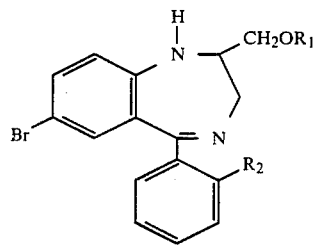

in which $R_1$ is a hydrogen atom or a lower alkoxy or alkanoyloxy radical and $R_2$ is a halogen atom. The compounds possess psychopharmacological, and especially anti-aggressive properties. To manufacture compounds of formula I, corresponding 2-halomethyl-7-bromo-5-(2-halophenyl)-1H-2,3-dihydro-1,4-benzodiazepines are cyclized to corresponding 7-bromo-1,2-methylene-5-(2-halophenyl)-1H-2,3-dihydro-1,4-benzodiazepines and in these the aziridine ring is opened through treatment with a lower alcohol or a lower carboxylic acid in the presence of a Lewis acid.

7 Claims, No Drawings

7-BROMO-5-(2-HALOPHENYL)-1H-2,3-DIHYDRO-1,4-BENZODIAZEPINE PHARMACEUTICALS

BACKGROUND OF THE INVENTION

The present invention relates to novel 7-bromo-5-(2-halophenyl)-1H-2,3-dihydro-1,4-benzodiazepine compounds, to pharmaceutical compositions containing these compounds, to a method of manufacturing these compounds, and also to intermediate compounds useful in manufacturing the compounds of the invention.

U.S. Pat. No. 3,998,809 and U.S. Pat. No. 4,096,141 describe 5-phenyl-1H-2,3-dihydro-1,4-benzodiazepine derivatives having a substituted methyl radical in the 2-position. These derivatives have properties which exert an influence on the central nervous system, in particular they have anticonvulsive and tranquillizing properties and also sedative and muscle-relaxant properties.

The novel compounds of the present invention fall within the general formulae given in the documents mentioned, but have not been described or named therein.

German Pat. No. 25 20 957 (=U.S. Pat. Nos. 4,098,786 and 4,244,869) describes 1-methyl-7-bromo-2-alkoxy-methyl-5-(2-halophenyl)-1H-2,3-dihydro-1,4-benzodiazepine compounds which likewise fall within the general formulae of the previously mentioned documents. It is known from these latter patents that, through the introduction of a bromine substituted group in the 7-position of the 1-methyl-5-phenyl-1,4-benzodiazepine structure, a particularly favorable efficacy profile is achieved. Thus, the preferred group of compounds, claimed in the German patent, namely 7-bromo-1-methyl-2-alkoxymethyl-5-(2-halophenyl)-1H-2,3-dihydro-1,4-benzodiazepines, is distinguished from the compounds set forth in the first mentioned documents, for example, the 7-chloro-compounds analogous to the 7-bromo-compounds, in their pharmacological profile through a clearly improved ratio between anticonvulsive, anxiolytic and antiaggressive effective components and sedative and muscle-relaxant effective components, which lead to undesirable side effects.

SUMMARY OF THE INVENTION

It is therefore an object of the present invention to provide novel 5-phenyl-1H-2,3-dihydro-1,4-benzodiazepine derivatives having an anxiolyticantiagressive effect but at the same time having an improved pharmacological efficacy profile.

In accomplishing the foregoing objects, there has been provided according to one aspect of the present invention a novel compound comprising a 7-bromo-5-(2-halophenyl)-1H-2,3-dihydro-1,4-benzodiazepine compound of the formula I:

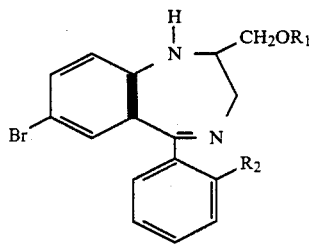

in which $R_1$ is a hydrogen atom, an alkyl radical having 1 to 3 carbon atoms, or an alkanoyl radical having 2 to 4 carbon atoms, and $R_2$ is a halogen atom, and the acid addition salts thereof.

In accordance with another aspect of the present invention, there has been provided a process for preparing the 7-bromo-5-(2-halophenyl)-1H-2,3-dihydro-1,4-benzodiazepine compounds defined above, comprising the steps of: cyclizing a 2-halomethyl-7-bromo-5-(2-halophenyl)-1H-2,3-dihydro-1,4-benzodiazepine compound of the formula III

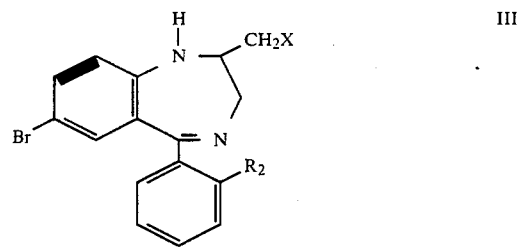

in which $R_2$ has the above-defined meaning, and X is a chlorine, bromine or iodine atom, or a mixture of such compounds by treatment with a strong base in an organic solvent which is inert under the reaction conditions, to form a 7-bromo-1,2-methylene-5-(2-halophenyl)-1H-2,3-dihydro-1,4-benzodiazepine of the formula II

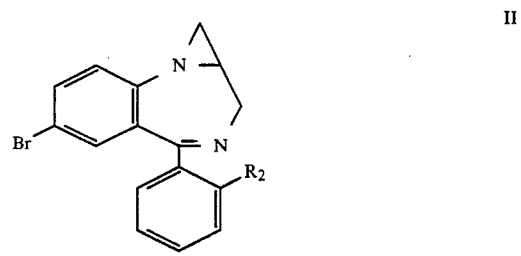

in which $R_2$ has the above-defined meaning; reacting the compound of formula II with a compound of formula IV,

$$R_1'-OH \qquad IV$$

in which $R_1'$ is an alkyl radical having 1 to 3 carbon atoms or an alkanoyl radical having 2 to 4 carbon atoms, in the presence of a Lewis acid to form a compound of the formula Ia

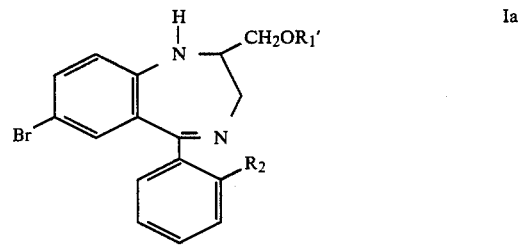

in which $R_1'$ has the above-defined meaning. In the case in which $R_1'$ is an alkanoyl radical having 2 to 4 carbon atoms, the process further comprises the optional step of hydrolyzing the ester of the general formula Ia to give a compound of the general formula Ib

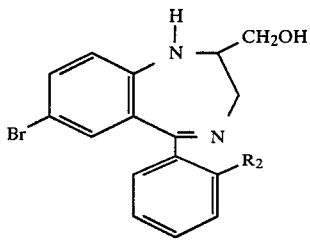

in which $R_2$ has the above-defined meaning.

In accordance with still another aspect of the invention, there has been provided a novel intermediate compound comprising a 7-bromo-1,2-methylene-5-(2-halophenyl)-1H-2,3-dihydro-1,4-benzodiazepine of the general formula II

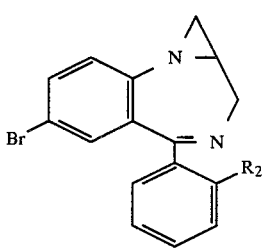

in which $R_2$ is a halogen atom, and the acid addition salts thereof.

Finally, the invention also provides a pharmaceutical composition comprising a compound as defined above and a solid or liquid pharmaceutical diluent or carrier.

Further objects, features and advantages of the present invention will become apparent from the detailed description of preferred embodiments which follows.

DETAILED DESCRIPTION OF PREFERRED EMBODIMENTS

This invention relates to novel 7-bromo-5-(2-halophenyl)-1H-2,3-dihydro-1,4-benzodiazepine compounds of the general formula I

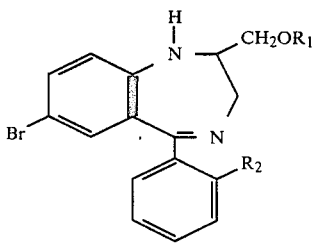

in which $R_1$ is a hydrogen atom, or an alkyl radical with 1 to 3 carbon atoms or an alkanoyl radical with 2 to 4 carbon atoms, and $R_2$ is a halogen atom, and their acid addition salts, to pharmaceutical compositions containing these compounds, and to a method for the manufacture of these compounds, as well as intermediate compounds useful in such manufacture. Preferably, $R_1$ is a hydrogen atom or an alkyl radical with 1 or 2 carbon atoms. The halogen substituent $R_2$ may be fluorine, chlorine or bromine, and is preferably chlorine.

It was found, surprisingly, that the novel 2-hydroxymethyl-, 2-alkanoyloxymethyl- and 2-alkoxymethyl-7-bromo-5-(2-halophenyl)-1H-2,3-dihydro-1,4-benzodiazepines of the present invention, which are unsubstituted in the 1-position, possess valuable psychopharmacological properties and exhibit marked anxiolytic-antiaggressive effects. They differ from the analogous 1-methyl-2-hydroxy-methyl- or 1-methyl-2-alkoxymethyl-7-bromo-5-(2-halophenyl)-1H-2,3-dihydroxy-1,4-benzodiazepines through a substantially more favorable efficacy profile.

Thus, the novel compounds which are unsubstituted in the 1-position are distinguished, in comparison with analogous 1-methyl compounds, by improved antiaggressive-anxiolytic effects, and in that the negative effects on muscular co-ordination and muscle tone are quite substantially reduced. Thus, the dosage ranges at which muscular co-ordination or muscle tone is affected are approximately twice or three times as high for the compounds of the present invention as for the corresponding 1-methyl compounds. The antiaggressive-anxiolytic effects of the present compounds, however, are evident in doses which are only approximately half as high as the doses which are required with the corresponding 1-methyl compounds. Consequently, a multiplication of the ratio between effective doses and the doses showing undesirable side effects is achieved. This favorable activity profile is of great value for using the compounds in the treatment of outpatients with psychic disorders.

The surprisingly favorable efficacy profile of the present compounds which are unsubstituted in the 1-position, in comparison with corresponding 1-methyl compounds, can be seen from the results of the pharmacological standard tests on mice described below. The compounds according to the invention and the analogous 1-methyl compounds were tested together with diazepam (commercial product: "Valium") as a comparison substance. The test results are given in the following Table wherein the effective doses of the test compounds each are indicated as a multiple of the respective effective doses of the standard compound diazepam.

DESCRIPTION OF THE PHARMACOLOGICAL TEST METHODS

1. Acute Toxicity

The acute 7-day toxicity is determined after a single application per os on the white NMRI mouse, on an empty stomach, and the $LD_{50}$ values are calculated by means of electronic data processing through a probit analysis.

2. Examination for anxiolytic and antiaggressive activity

Determination of the effective dose for the inhibition of aggression in the mouse, brought about through isolation. Before the test the mice are kept in strict isolation for four weeks in a solitary cage. After this period, the mice kept in isolation spontaneously attack mice which are added to the cage and which have not been kept in isolation. The test substances are administered orally to the isolated mice, and after 60 minutes the dose is determined, which leads to a 50% reduction in the aggressive behavior ($ED_{50}$). The results obtained in this test arrangement (modified according to Weischer and Opitz, Arch.int. Pharmacodyn.195,252 (1972)) are a good indication of the anxiety stress and tension relieving properties of the compounds.

3. Examination for muscular coordination impairing activity

The ability of muscular coordination is determined in the mouse by the rotating rod test according to Blum (1973).

For this test, only male NMRI mice are used, which can support themselves for five minutes on a rotating rod with a diameter of 4 cm at a rotational speed of 12 rotations per minute.

The test substances are administered orally to the animals one hour before the commencement of the test in the form of a 2% suspension in tylose solution. The animals are each placed twice for a period of 60 seconds onto the rotating rod. Animals which cannot support themselves on the rotating rod for a total of 110 seconds are regarded as having impaired muscular coordination. The dose which brings about an impairment in 50% of the animals is regarded as the $ED_{50}$.

4. Evaluation of the muscle relaxant activity in the traction test on the mouse (Arzneimittelforschung 17,561 (1967)).

In this test the influence of the test substances on the muscle tone is evaluated. The test substance is administered orally to mice. After 120 minutes the mice are suspended by their front paws on a thin, horizontally taut wire. The dose at which exactly half the animals fail to also grasp the wire with their hind paws within 5 seconds is regarded as the $ED_{50}$.

The results of the test experiments are given in the following Table. In columns 2 to 4, in each case the quotients from the $ED_{50}$ values of the test substances divided by the respective $ED_{50}$ value of diazepam are indicated, i.e. the effective diazepam doses were set equal to 1 and the effective doses of the other test substances were indicated as a multiple of this.

In columns 5 and 6 of the Table, the quotients which result from dividing the doses impairing muscular coordination or muscle tone by the anxiolytically effective doses are indicated. These quotients show that the doses in which negative musculotropic properties of the compound according to the invention come into effect are many times higher than the doses with anxiolytic-antiaggressive effect, and that the ratio between both doses with the compounds according to the invention is substantially higher than with the analogous 1-methyl-compounds.

The compounds of Formula A were tested

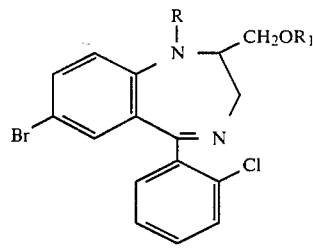

A in which $OR_1$ and R have the meanings indicated in the following Table.

| Test Substance of Formula A | 1<br>Acute Toxicity $LD_{50}$ mg/kg p.o. mouse | 2<br>Inhibition of aggression caused by isolation* | 3<br>Disturbance to muscular coordination in the revolving bar test* | 4<br>Disturbance to muscle tone in the Test de la Traction* | 5<br>Quotient $\frac{3}{2}$ | 6<br>Quotient $\frac{4}{2}$ |
|---|---|---|---|---|---|---|
| Substance Ex 2 ($OR_1 = OCH_3$ R = H) | 1330 | 0.59 | 3.17 | 32.0 | 5.38 | 54.2 |
| 1-$CH_3$ analogous comparison substance ($OR_1 = OCH_3$ R = $CH_3$) | >1470 | 1.17 | 1.30 | 8.63 | 1.11 | 7.38 |
| Substance Ex 4 ($OR_1 = OH$ R = H) | >1370 | 0.26 | 2.23 | 42.6 | 8.60 | 164 |
| 1-$CH_3$ analogous comparison substance ($OR_1 = OH$ R = $CH_3$) | >1470 | 0.65 | 0.87 | 25.2 | 1.3 | 38.8 |
| Diazepam | 850 | 1 | 1 | 1 | 1 | 1 |

*$ED_{50}$ mg/kg Test substance: $ED_{50}$ mg/kg Diazepam

It was also found that in contrast to other previously known pharmacologically active benzodiazepines, the present compounds, which have a free NH-function in the 1-position of the ring structure—possibly after setting free the OH-group from a possible acyloxy- or alkoxy lateral chain—can be directly conjugated with glucuronic acid and in conjugated form can be directly excreted without previously undergoing a more extensive metabolisation. This means that metabolism and in particular liver enzymes are much less burdened through intake of the present compounds than through other benzodiazepine derivatives, which have to be metabolized prior to excretion. This is of significance particularly in long-term therapy, as must in fact frequently be employed in the treatment of people with psychic disorders. Through the ease of elimination of the compounds, the risk of accumulation is practically excluded even with treatment of long duration.

According to another aspect of the present invention, the compounds of Formula I are manufactured by a method in which a 2-halomethyl-7-bromo-5-(2-halophenyl)-1H-2,3-dihydro-1,4-benzodiazepine compound of the general formula III

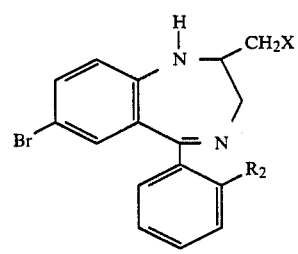

III in which $R_2$ has the above defined meaning, and X is a chlorine, bromine or iodine atom, or a mixture of such compounds is cyclized by treatment with a strong base in an organic solvent which is inert under the reaction conditions to form a 7-bromo-1,2-methylene-5-(2-halophenyl)-1H-2,3-dihydro-1,4-benzodiazepine of the general formula II

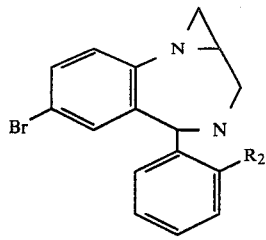

II in which $R_2$ has the above defined meaning. Subsequently for manufacturing a compound of the general formula Ia

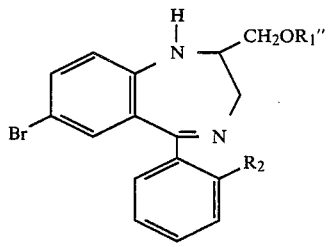

Ia in which $R_2$ has the above defined meaning, and $R_1''$ is an alkyl radical with 1 to 3 carbon atoms, the compound of formula II is reacted in the presence of a Lewis acid with an alcohol of the formula IV'

 IV' in which $R_1''$ has the above meaning, or for manufacturing a compound of the general formula Ia''

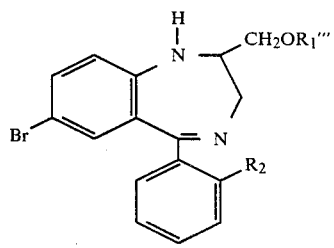

Ia'' in which $R_1'''$ is an alkanoyl radical with 2 to 4 carbon atoms and $R_2$ has the above defined meaning, the compound of formula II is reacted in an organic solvent which is inert under the reaction conditions in the presence of a Lewis acid with a lower aliphatic carboxylic acid of the general formula IV'''

 IV''' in which $R_1'''$ has the above meaning, and the ester obtained of the general formula Ia'' may be hydrolysed to a compound of the general formula Ib

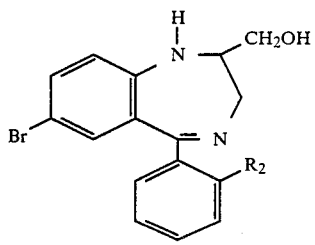

Ib in which $R_2$ has the above defined meaning. If the compound of formula I is obtained in the form of the free compound, it may be converted into an acid addition salt. If the compound of formula I is obtained in the form of an acid addition salt, the latter may be converted into the free compound of formula I.

The present method is surprising in many respects. It is indeed known that aziridine rings can be formed from aliphatic beta-haloalkylamines. However, it was not to be expected that the compound of the formula III, which represents a phenylogous amidine (and which therefore does not have a basic amine function, but possesses an imino-function rich in electrons) could be reacted to form a 1,2-methylene bridge and be converted into a stable compound with a ring system, in which an aziridine ring is fused to the benzodiazepine structure.

It is also surprising that the subsequent opening of the aziridine ring takes place exclusively at the desired position, i.e. exclusively leads to the 7-membered ring of the benzodiazepine structure being substituted in the 2-position.

The cyclization of the 2-halomethyl compound of formula III to form a compound of formula II is expediently carried out in a solvent which is inert under the reaction conditions, in the presence of a strong base at elevated temperature, for example, at a temperature of from 50° to 150° C. Suitable strong bases are, for example, alkali metal lower alcoholates, such as, for example, sodium methylate, sodium ethylate or sodium tertiary butylate or alkali metal- or alkaline earth metal hydrides, such as, for example, sodium hydride, lithium hydride or calcium hydride. Suitable inert solvents are, for example, lower alcohols, aromatic hydrocarbons such as toluene or xylene, dimethylformamide or mixtures of such solvents. Thus, for example, when using alkali metal alcoholates, the corresponding alcohols are particularly suitable as solvents, and when using metal hydrides, aromatic hydrocarbons or dimethylformamide are particularly suitable as solvents.

The opening of the aziridine ring of the compound of formula II takes place by reaction of the compound of the formula II with a lower alcohol of the formula IV', which may be methanol, ethanol, n-propanol or isopropanol, or with an acid of the formula IV''', preferably acetic acid or propionic acid, in the presence of a Lewis acid and a solvent. In the case of the reaction with a lower alcohol, the alcohol itself can serve as the solvent. If desired, further organic solvents which are inert under the reaction conditions, for example, halogenated hydrocarbons, such as methylene chloride, or aromatic hydrocarbons, such as toluene or xylene, or aliphatic or aromatic ethers, for example, diethyl ether or tetrahydrofuran may be added. In the case where the reaction is effected with a lower carboxylic acid, it is expedient to add one of the above mentioned solvents. Particularly suitable Lewis acids are boron halides, such as borontrichloride or, preferably, borontrifluoride. The conversion can take place at a temperature of from 0° to 30° C., preferably at room temperature.

The esters of formula Ia'' obtained by the reaction of the compound of formula II with a lower aliphatic carboxylic acid, can be hydrolysed in a manner known per se. Expediently, the ester is subjected to an alkaline hydrolysis, for example, by means of an inorganic base such as an alkali metal hydroxide or carbonate, for example, sodium hydroxide, potassium hydroxide or sodium carbonate. The reaction expediently takes place at elevated temperature, preferably at the boiling temperature of the reaction mixture. If desired, organic solvents which are miscible with water, preferably lower alcohols, such as methanol or ethanol, can be added.

The compounds of the formula I can be isolated from the reaction mixture and purified in a manner known per se. If the compounds are in the form of their acid addition salts, these can be converted in the usual manner into the free bases and these in turn can be converted, if desired, in a known manner into pharmacologically compatible acid addition salts.

Suitable pharmacologically acceptable acid addition salts of the compounds of formula I are, for example, salts with inorganic acids, such as hydrochloric acid, hydrobromic acid, sulphuric acid and phosphoric acid, or salts with organic acids, such as, for example, maleic acid, furmaric acid, acetic acid, benzoic acid, methane sulphonic acid, cyclohexylaminosulphonic acid, lactic acid, tartaric acid and phenylacetic acid.

The starting compound of formula III can be obtained, by demethylating compounds of the formula V

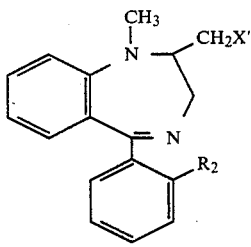

in which $R_2$ has the above defined meaning, and $X'$ is a chlorine or bromine atom, in a known manner by reaction with hydrogen iodide, to result in compounds of the formula VI

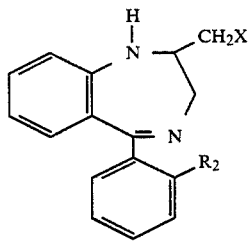

in which $R_2$ and X have the above defined meanings, and the compounds of formula VI are then brominated in a manner known per se.

The compounds of formula V can be obtained in a known manner, for example, according to the methods described in German Offenlengungsschriften Nos. 22 21 558 or 23 53 187 or in German Pat. No. 25 20 937, by treating $N_1$-phenyl-$N_1$-methyl-$N_2$-(2-halophenyl)-2-hydroxy-1,3-diaminopropane with a phosphorus oxyhalide, preferably phosphorus oxychloride, and subsequent isomerization of the resulting cyclisation mixture.

The de-methylation of the compounds of the formula V by means of hydriodic acid can take place in a manner known per se. Expediently, the reaction is carried out with concentrated hydriodic acid, optionally in the presence of a solvent which is inert under the reaction conditions, for example, a lower aliphatic carboxylic acid, such as acetic acid, at a temperature of from 50° to 100° C.

In the reaction, the halogen in the lateral chain is partially substituted by iodine, so that a mixture of halides of formula VI results. This can be used for the further reaction without separation.

The bromination of the compounds of the formula VI can take place in a manner known per se using N-bromosuccinimide in a solvent which is inert under the reaction conditions, for example, a halogenated hydrocarbon, such as methylene chloride.

Owing to their pharmacological properties described above, the new compounds according to the invention constitute valuable psychopharmaceutical compounds.

For utilization in pharmaceutical compositions, both the free bases and their pharmacologically acceptable acid addition salts can be used. The compounds of formula I or their physiologically compatible acid addition salts, together with usual solid or liquid pharmaceutical diluents or carriers, can be contained in pharmaceutical forms of presentation, such as, for example, tablets, capsules, suppositories or solutions. These preparations can be manufactured according to methods known per se, using conventional solid carrier substances, such as, for example, lactose, starch or talcum or liquid diluents, such as, for example, water, fatty oils or liquid paraffins. These pharmaceutical preparations can contain from 1 to 50 mg active substance per individual dose. The dose used is of course adapted to the species to be treated and to individual requirements.

The following non-limiting Examples illustrate the manufacture of the new compounds.

EXAMPLE 1

7-Bromo-1,2-methylene-5-(2-chlorophenyl)-1H-2,3-dihydro-1,4-benzodiazepine (A) 50 g N-methyl-N-(2-hydroxy-3-(2-chlorobenzoylamino)-propyl)aniline are boiled in 250 ml phosphorus oxychloride for 2.5 hours under reflux. Then the surplus phosphorus oxychloride is distilled off and the residue is poured onto a mixture of 300 g ice and 300 ml water. Then the reaction product is extracted three times with in each case 200 ml chloroform. The chloroform phase is washed with 200 ml water and subsequently shaken with dilute sodium hydroxide (20%) solution until an alkaline reaction is obtained. The chloroform phase is washed until neutral with water, dried over sodium sulphate and after filtering is evaporated in a vacuum. For further purification, the residue (45.1 g) is dissolved in ether and filtered off from the resulting precipitate. After distilling off the ether, 35.8 g of a mixture of 1-methyl-3-chloro-6-(2-chlorophenyl)-1,2,3,4,-tetrahydro-1,5-benzodiazocine and 1-methyl-2-chloromethyl-5-(2-chlorophenyl)-2,3-dihydro-1H-1,4-benzodiazepine is obtained. In order to isomerise the benzodiazocine component of the cyclisation mixture, the latter is dissolved in 150 ml tetrachloroethane and the solution is boiled for 30 minutes under reflux. After distilling off the solvent, 35.2 g 1-methyl-2-chloromethyl-5-(2-chlorophenyl)-2,3-dihydro-1H-1,4-benzodiazepine are obtained, which can be used in the following reaction without further purification.

(B) 50 g 1-methyl-2-chloromethyl-5-(2-chlorophenyl)-1H-2,3-dihydro-1,4-benzodiazepine are dissolved in 93 ml acetic acid, the solution is mixed with 150 ml hydriodic acid (65%) and heated for four hours to 80° C. The reaction solution is then cooled down and poured onto 500 g ice. After the melting of the ice, the reaction product is extracted with methylene chloride and the organic phase is mixed with ice-cold sodium hydroxide solution (10%) until an alkaline reaction is obtained. The methylene chloride phase is then separated, washed until neutral, dried over sodium sulphate, filtered and the solvent removed in vacuum. The residue is 56 g oily crude product which is a mixture of 80% 2-chloromethyl-5-(2-chlorophenyl)-1H-2,3-dihydro-1,4-benzodiazepine and 20% 2-iodomethyl-5-(2-chlorophenyl)-1H-2,3-dihydro-1,4-benzodiazepine.

(C) 120 g of the mixture obtained as described above are dissolved in 900 ml methylene chloride, the solution is mixed with 58 g N-bromosuccinimide and stirred overnight at room temperature. The reaction solution is then washed with water, then with 10% sodium carbonate solution, and again with water, dried over sodium sulphate, filtered and the solvent distilled off. The residue is 111 g crude product, which contains a mixture of approximately 80% 2-chloromethyl-7-bromo-5-(2-chlorophenyl)-1H-2,3-dihydro-1,4-benzodiazepine and 20% 2-iodomethyl-7-bromo-5-(2-chlorophenyl)-1H-2,3-dihydro-1,4-benzodiazepine.

For conversion into the hydrochloride, this crude product is dissolved in acetone and mixed with a solution of hydrogen chloride gas in ether. The separated crystals are filtered off and recrystallized repeatedly from ethanol/acetone. 61 g 2-chloromethyl-7-bromo-5-(2-chlorophenyl)-1H-2,3-dihydro-1,4-benzodiazepine hydrochloride are obtained with a melting point of 240° to 243° C., which contain 10% of the analogous 2-iodomethyl compound.

(D) 42 g of this 7-bromo-2-chloromethyl-5-(2-chlorophenyl)-1H-2,3-dihydro-1,4-benzodiazepine hydrochloride are dissolved in 100 ml methanol and mixed with a solution of 9.6 g sodium in 320 ml methanol, and the reaction mixture is boiled for two hours under reflux. After cooling, the reaction mixture is poured into 400 ml water, crystalline 7-bromo-1,2-methylene-5-(2-chlorophenyl)-1H-2,3-dihydro-1,4-benzodiazepine is filtered off and re-crystallized from acetone. Melting point 172° to 174° C., yield 29.4 g.

EXAMPLE 2

7-Bromo-2-methoxymethyl-5-(2-chlorophenyl)-1H-2,3-dihydro-1,4-benzodiazepine 25 g 7-bromo-1,2-methylene-5-(2-chlorophenyl)-1H-2,3-dihydro-1,4-benzodiazepine are dissolved in 270 ml methanol and the solution is mixed, under stirring and cooling at 20° to 30° C. with 52 ml borontrifluoride-etherate. The reaction mixture is stirred for two hours at room temperature and is then diluted with 500 ml toluene. The toluene solution is washed with saturated sodium carbonate solution and then washed with water, dried over sodium sulphate, filtered and the solvent distilled off. The residue is 31 g of crude 7-bromo-2-methoxymethyl-5-(2-chlorophenyl)-1H-2,3-dihydro-1,4-benzodiazepine. This residue is dissolved in ether and mixed with a solution of hydrogen chloride gas in ether. The separated hydrochloride crystals are filtered off and extracted three times with a mixture of acetone and a little ethanol. 42.9 g 7-bromo-2-methoxymethyl-5-(2-chlorophenyl)-1H-2,3-dihydro-1,4-benzodiazepine hydrochloride are obtained.

EXAMPLE 3

7-Bromo-2-acetoxymethyl-5-(2-chlorophenyl)-1H-2,3-dihydro-1,4-benzodiazepine 55 g 7-bromo-1,2-methylene-5-(2-chlorophenyl)-1H-2,3-dihydro-1,4-benzodiazepine are dissolved in 450 ml methylene chloride, and 180 ml acetic acid are added to the solution. Then, under cooling to 0° C., 110 ml borontrifluoride-etherate are slowly dropped in. The reaction mixture is stirred for a further hour at room temperature and is then poured onto a mixture of ice and water. The organic phase is separated off and washed with water, then with dilute sodium hydroxide (10%) and again with water, dried over sodium sulphate, filtered and evaporated. The residue is 68 g crude 7-bromo-2-acetoxymethyl-5-(2-chlorophenyl)-1H-2,3-dihydro-1,4-benzodiazepine.

EXAMPLE 4

7-Bromo-2-hydroxymethyl-5-(2-chlorophenyl)-1H-2,3-dihydro-1,4-benzodiazepine 68 g crude 7-bromo-2-acetoxymethyl-5-(2-chlorophenyl)-1H-2,3-dihydro-1,4-benzodiazepine (Example 3) are boiled, without further purification, with 640 ml of a solution of potassium hydroxide in methanol (15%) for one hour under reflux. Then the solvent is distilled off and the residue taken up in water and extracted with ether. After the usual working up of the ether phase, 53 g of crude 7-bromo-2-hydroxymethyl-5-(2-chlorophenyl)-1H-2,3-dihydro-1,4-benzodiazepine are obtained. In order to convert the compound into its hydrochloride a solution of this crude alcohol in ether is mixed with a solution of hydrogen chloride gas in ether and the precipitated 7-bromo-2-hydroxymethyl-5-(2-chlorophenyl)-1H-2,3-dihydro-1,4-benzodiazepine hydrochloride is isolated. Melting point 228° to 232° C., yield 26.1 g.

EXAMPLE 1: TABLETS

Tablets are produced having the following composition per tablet:

| | |
|---|---|
| 6-bromo-2-hydroxymethyl-5-(2-chlorophenyl)-1H—2,3-dihydro-1,4-benzodiazepine-hydrochloride | 25 mg |
| Corn starch | 60 mg |
| Lactose | 130 mg |
| Gelatine (10% solution) | ·6 mg |

The active substance, the maize starch and the lactose are thickened with the 10% gelatine solution to form a paste which is comminuted, and the resulting granulated material is brought onto a suitable plate and dried at 45° C. The dried granulate is passed through a crushing machine and mixed in a mixer with further adjuvants as follows:

| | |
|---|---|
| Talcum | 5 mg |
| Magnesium stearate | 5 mg |
| Corn starch | 9 mg |

What is claimed is:

1. A 7-bromo-5-(2-halophenyl)-1H-2,3-dihydro-1,4-benzodiazepine compound of the formula I:

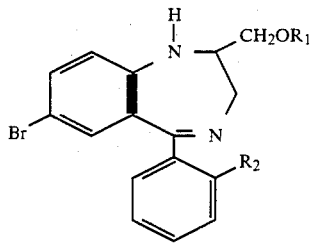

in which $R_1$ is a hydrogen atom, a methyl or ethyl radical, or an acetyl radical, and $R_2$ is a chlorine atom, and acid addition salts thereof.

2. A compound as defined in claim 1, in the form of an acid addition salt with a pharmacologically-acceptable acid.

3. A compound according to claim 1 wherein $R_1$ is hydrogen, methyl or acetyl and acid addtion salts thereof.

4. A compound according to claim 3 wherein $R_1$ is a hydrogen atom and acid addition salts thereof.

5. A compound according to claim 3 wherein $R_1$ is a methyl group and acid addition salts thereof.

6. A compound according to claim 3 wherein $R_1$ is an acetyl group and acid addition salts thereof.

7. A pharmaceutical composition, comprising a compound as claimed in claim 1 and a solid or liquid pharmaceutical diluent or carrier.